United States Patent [19]
Murray

[11] Patent Number: 6,093,188
[45] Date of Patent: Jul. 25, 2000

[54] ADJUSTABLE BONE FIXATION PLATE

[76] Inventor: William M. Murray, 2650 Spring Hill La., Enola, Pa. 17025

[21] Appl. No.: 08/966,630

[22] Filed: Nov. 10, 1997

[51] Int. Cl.$^7$ .................................................. A61B 17/80
[52] U.S. Cl. .............................................................. 606/69
[58] Field of Search .............................. 606/69, 70, 71, 606/61, 72, 73, 105

[56] References Cited

U.S. PATENT DOCUMENTS

| | | |
|---|---|---|
| 2,580,821 | 1/1952 | Nicola ........................................ 606/69 |
| 2,684,070 | 7/1954 | Kelsey . |
| 2,780,223 | 2/1957 | Haggland . |
| 3,807,394 | 4/1974 | Attenborough ............................ 606/71 |
| 3,939,828 | 2/1976 | Mohr et al. . |
| 4,444,181 | 4/1984 | Wevers et al. . |
| 4,456,006 | 6/1984 | Wevers et al. . |
| 4,905,679 | 3/1990 | Morgan . |
| 4,957,496 | 9/1990 | Schmidt ..................................... 606/70 |
| 5,007,921 | 4/1991 | Brown . |
| 5,026,390 | 6/1991 | Brown . |
| 5,449,359 | 9/1995 | Groiso . |
| 5,468,242 | 11/1995 | Reisberg . |
| 5,478,354 | 12/1995 | Tovey et al. . |
| 5,690,631 | 11/1997 | Duncan et al. ............................ 606/69 |
| 5,752,958 | 5/1998 | Wellisz ..................................... 606/69 |
| 5,766,176 | 6/1998 | Duncan .................................... 606/69 |

FOREIGN PATENT DOCUMENTS

| | | |
|---|---|---|
| 0 433 852 | 3/1996 | European Pat. Off. . |
| 92 13802 | 7/1994 | France . |
| 3412769 | 10/1985 | Germany . |
| 44 18 159 | 9/1995 | Germany . |
| 335797 | 3/1959 | Switzerland . |
| 1102585 | 7/1984 | U.S.S.R. . |
| 1579575 | 11/1980 | United Kingdom . |

*Primary Examiner*—Guy V. Tucker
*Attorney, Agent, or Firm*—Thomas Hooker, P.C.

[57] ABSTRACT

A bone plate includes a pair of mounting portions with bridges extending between the mounting portions. Each bridge includes at least one spring member and a compression member, arranged in series.

30 Claims, 3 Drawing Sheets

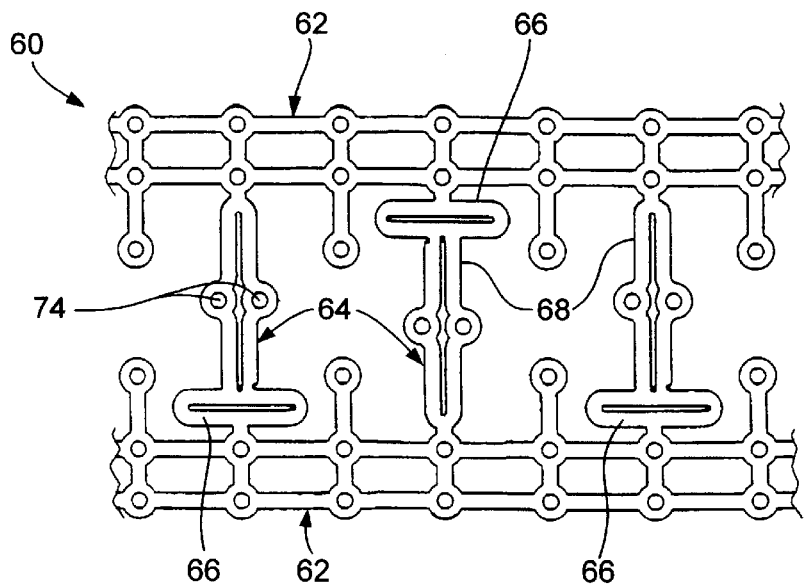
FIG. 5
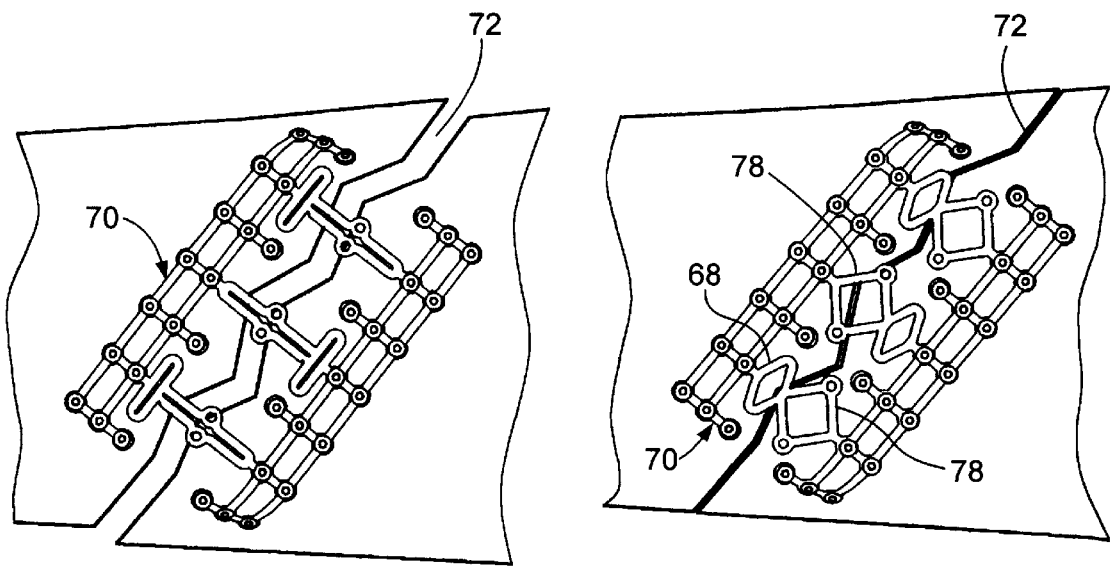
FIG. 6
FIG. 7

ADJUSTABLE BONE FIXATION PLATE

FIELD OF THE INVENTION

The invention relates to bone plates used to fixate and compress fractures during healing.

DESCRIPTION OF THE PRIOR ART

The prior art includes rigid bone plates which are secured to the ends of bone segments and extend across fractures. With these plates, it is difficult to assure that the fracture is fully closed when the plate is mounted on the bone segments, conventionally by screws. Rigid bone plates isolate the fracture from stresses during healing. Stress applied to one of the segments during healing can be largely transmitted to the other segment directly through the plate, and not through the fracture. Isolation of the fracture from stress can prevent proper healing of the fracture.

Metal bone plates have been described with anchor portions which are secured to both bone segments and with deformable portions which extend across the fracture. The deformable portions are bent to reduce the distance between the anchor portions and close the fracture. The bending is performed by a tool which is removed after the fracture is closed. However, when the tool is removed the bent portion of the plate rebounds a short distance, so that compression of the fracture cannot be achieved. Compression of the fracture during healing is important to maximize stability of fixation and to promote strong bone growth across the fracture site.

Resilient spring clips have been proposed for closing bone fractures. These clips are small resilient members which are individually applied to the bone segments and extend across the fracture. A number of clips are required to close a fracture. The clips include points which are driven into the bone segments to either side of the fracture. The clips must be spread apart prior to attachment to the bone segments.

SUMMARY OF THE INVENTION

The invention is a bone plate which is mounted on bone segments and extends across a fracture between the bone segments. The plate includes one or more bridges which extend across the fracture. The bridges include a compression member and a spring member, arranged in series. The compression member is foreshortened by a tool which permanently bends the member. When the tool is removed from a member the member rebounds and lengthens slightly. The compression member is shortened by the tool sufficiently to close any gap at the fracture and bring the bone segments into forcible engagement with each other and to elastically elongate the spring. The spring is elongated sufficiently to take up the rebound elongation of the compression member and still maintain a force holding the bone segments together during healing.

The plate includes a number of bridges spaced along the fracture. The compression members in the bridges are foreshortened distances appropriate to close any gap at the bridge and to assure that the spring members are placed under tension. The elasticity of the springs provides a compressive force at the fracture which stabilizes the fracture fragments and promotes healing.

Additionally, the resiliency of the bridges extending across the fracture permits local stresses applied to either bone segment to be transmitted at least partially between the segments across the fracture, to promote strong bone growth at the fracture.

Fracture of a bone may result in more than two bone fragments at the fracture site. This situation is commonly termed "comminution." The large number of mounting apertures in the anchor portions of the plate facilitate locating the plate on the bone segments with a mounting aperture over a bone fragment, thereby permitting securing the plate to the fragment to hold the fragment in place during healing. Physical manipulation of bone fragments relative to a mounted plate is facilitated by openings formed through the thickness of the plate, both adjacent the bridges and in the anchor portions. Surgical instruments may be extended through the openings to position bone fragments prior to securing the fragments to the anchor portions.

Other objects and features of the invention will become apparent as the description proceeds, especially when taken in conjunction with the accompanying drawings illustrating the invention, of which there are 3 sheets and two embodiments.

DESCRIPTION OF THE DRAWINGS

FIG. 5 is a view similar to FIG. 1 showing a portion of a second embodiment bone plate; and FIGS. 6 and 7 are views similar to FIGS. 3 and 4 showing compressing a fracture using the second embodiment bone plate.

DESCRIPTION OF THE PREFERRED EMBODIMENTS

Figure 1:
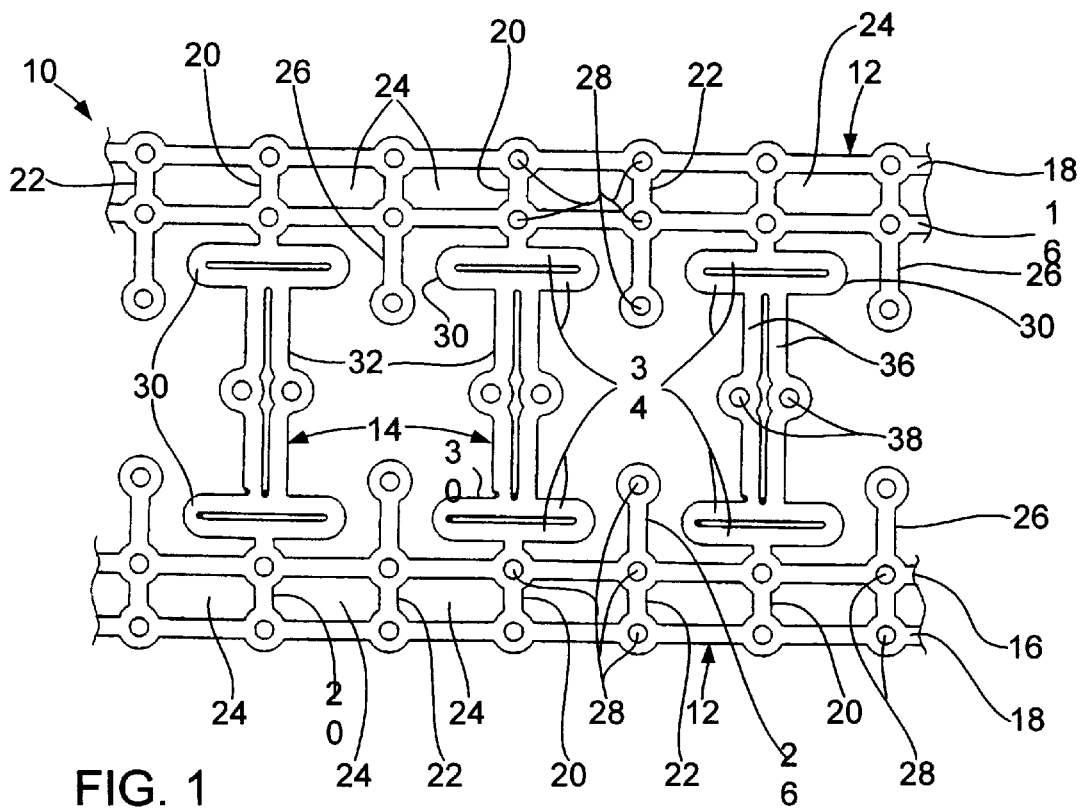
FIG. 1 is a view of a portion of a section of a bone plate per the invention.

FIG. 1 illustrates a portion of a section of a bone plate 10. A pair of like elongate anchor portions 12 extend longitudinally along opposed sides of the bone plate 10 and a plurality of spaced apart bridges 14 extend laterally across the plate 10 and join anchor portions 12. Bone plate 10 is manufactured from sheets of titanium, stainless steel or other biocompatible material, preferably by a laser cutting or stamping operation. Bone plates are manufactured in a range of sizes, and with a varying number of bridges as required to close particular bone fractures.

Each anchor portion 12 includes elongate inner and outer strips 16 and 18 which are joined together at regular intervals by laterally extending rungs 20 and 22. Rungs 20 join strips 16 and 18 together at bridges 14 to facilitate strong anchoring of the ends of the bridges 14. Rungs 22 are located between adjacent rungs 20. The rungs 20 and 22 define relatively large openings 24 extending through the anchor portions and spaced along the portions. Surgical instruments may be extended through openings 24 and the openings adjacent the bridges to manipulate bone fragments located under the openings after mounting of a bone plate across a fracture, as required. Rung extensions 26 extend inwardly of inner strips 16 at rungs 22, between adjacent bridges 14.

Small diameter mounting holes or apertures 28 are provided in the anchor portions 12 at the intersections of the rungs and strips and at the ends of rung extensions 26. The large number of apertures 28 permits rigid mounting of the anchor portions to bone segments.

Each bridge 14 includes a pair of resilient spring members 30 and a compression member 32, arranged in series between the anchor portions 12. As illustrated, the spring members are integrally joined to the inner strips 16 of adjacent anchor portions 12 and the compression members 32 are integrally joined to the inner portions of the spring members.

Each spring member 30 includes two closely spaced parallel strips 34 joined at the strip ends. The strips extend longitudinally along the plate 10. The middle of the outer spring strip 34 is joined to the inner anchor portion strip 16 and the middle of the inner strip 34 is joined to one end of the adjacent compression member 32. Each compression member 32 includes a pair of closely spaced parallel strips 36 which extend laterally across plate 10 between the centers or middles of the inner strips 34 of adjacent spring members 30. Spreading apertures 38 are provided in the centers of strips 36.

Figure 3:
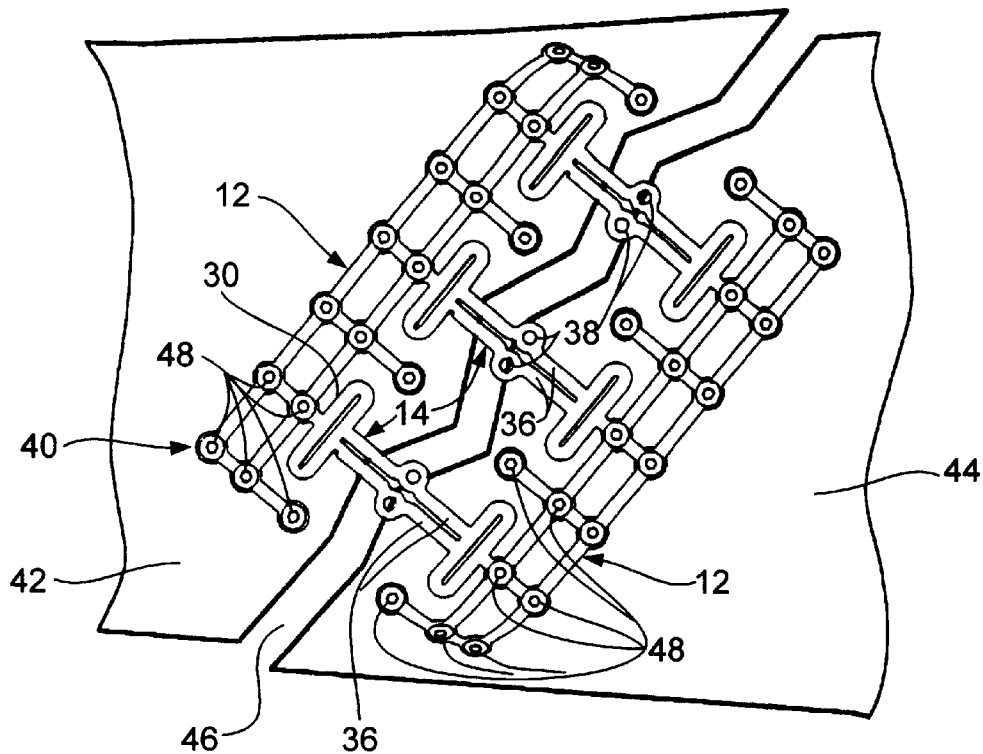
FIGS. 3 and 4 show a bone plate per FIG. 1 mounted on bone segments and extending across a fracture before and after compression of the fracture.
Figure 4:
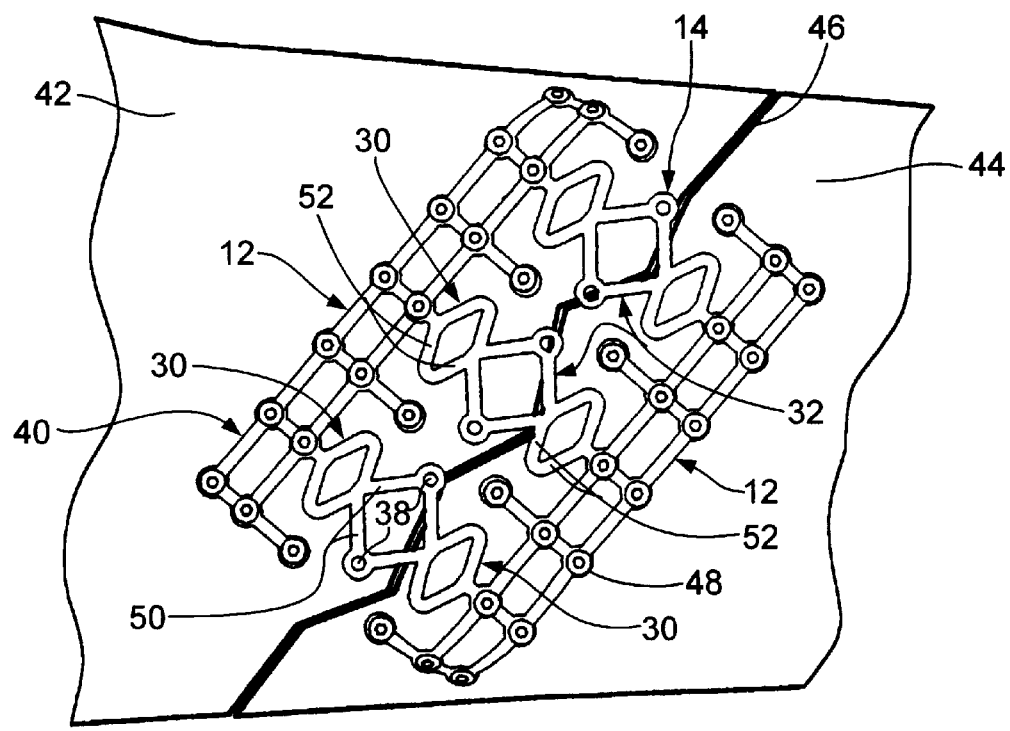

The bone plate is made from uniform thickness biocompatable sheet material, which may be titanium or stainless steel. As shown in FIGS. 3 and 4, an appropriate bone plate 40 is selected and is shaped by the surgeon to conform to the bone segments 42 and 44 located to either side of fracture 46. In practice, the gap at fracture 46 is less than illustrated. The bone plate is bent to conform to the surface of the bone segments 42 and 44 to either side of the fracture with the mounting apertures 28 resting flush against the surfaces of the bone segments. The plate is mounted with the anchor portions on bone and extending along the fracture and the bridges extending across the fracture. With the fracture reduced, the plate is put in place, as illustrated in FIG. 3. Then, bone pins 48 are inserted through apertures 28 and into the bone segments 42 and 44 to either side of the fracture 46 to mount each anchor portion 12 securely to bone segments 42, 44. The bone pins 48 may be threaded or unthreaded. If necessary, holes may be predrilled through apertures 28 into the hard cortical bone of segments 42 and 44. The large number of apertures 28 in each anchor portion 12 permits a large number of bone pins 48 to firmly hold each anchor portion to a bone segment so that the plate does not move relative to the bone segments during compression and healing of the fracture, despite stress applied to the anchor portions.

The bone fracture shown in FIGS. 3 and 4 is representational. In practice, may be fractured into comminution fragments adjacent the main fracture 46. These fragments of bone may be broken away from each bone segment. The large number of mounting apertures provided in each anchor portion permits a surgeon to adjust the location of plate 40 on the bone segments so that mounting hole apertures 28 are located over comminution fragments. In this way, a pin may be driven into each fragment to secure the fragments in place in order to further stabilize the fracture during healing. The movement of bone fragments to proper locations is facilitated by extending an instrument through the openings 24 in each anchoring portion and the interior space between the bridges 14, as illustrated in FIG. 3.

After mounting of bone plate 40 on bone segments 42 and 44 as shown in FIG. 3, fracture 46 is compressed by reducing the length of the bridges 14 extending across the fracture. The bridges 14 are preferably reduced in length starting at one end of the fracture and working to the other end of the fracture to progressively compress the fracture.

The length of the bridges is reduced by inserting tips of a spreading tool in the two spreading apertures 38 of each compression member 32 and moving the tips of the spreading tool apart to spread apart and permanently deform parallel strips 36. Each straight strip 36 is bent outwardly to form a convex, V-shaped strip 50 with the spreading aperture 38 located at the tip of the V-strip. The bent strips 50 reduce the length of the compression members. When the spreading tool is removed from strips 50 the strips rebound slightly and the members 32 therefore lengthen a short distance.

Spreading and permanent deformation of strips 36 foreshortens the strips, reduces the length of bridges 14, draws the bone segments 42 and 44 together to compress fracture 46 and elastically spreads apart strips 34 of the two spring members 30 to form elastic V-strips 52. The elastically stressed spring members 30 collapse partially in response to recoil of the compression member, but remain stressed to hold the fracture compressed during healing. The foreshortening of the compression member 32 is greater than sum of the width of the fracture 46 at is the bridge and the rebound distance of the compression member when the tool is withdrawn.

With plate 40 mounted on the bone segments 42 and 44 as shown in FIG. 4, the springs 30 and compression members 32 in the bridges permit limited relative movement of the bone segments at gap 46 in response to local stresses applied to the fractured bone to promote healing at the fracture. The continuous compressive force applied by plate 40 holds the segments together and allows limited relative movement between the joined bone segments in response to local stress.

Figure 2:
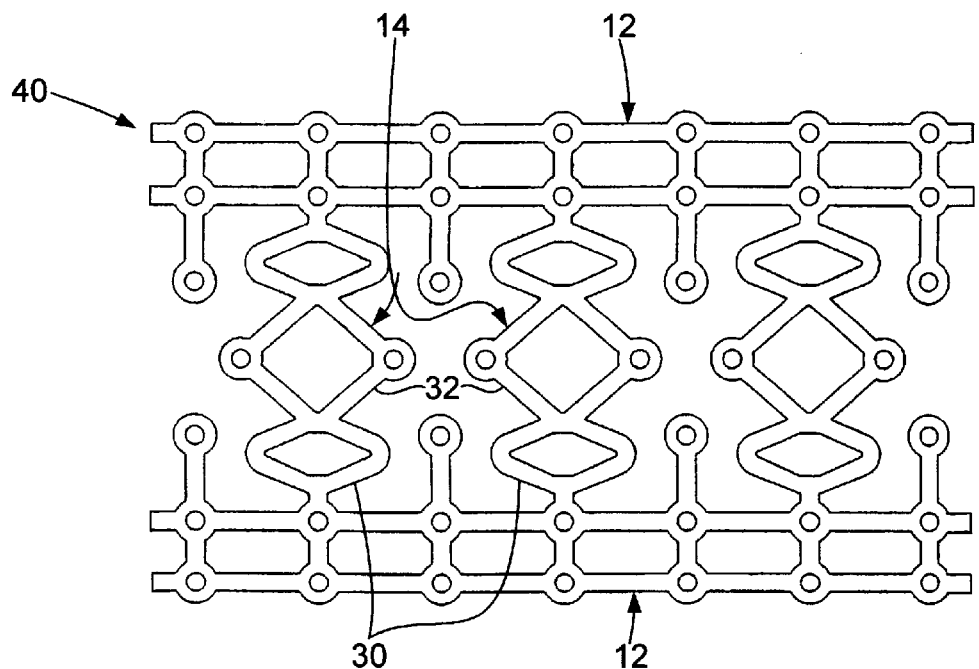
FIG. 2 is similar to FIG. 1 showing a plate with the bridges foreshortened.

In bridges 14 spring members 30 have the same spring constant and are located between compression members 32 and anchor portions 12. This arrangement locates the spreading apertures 38 in the compression member equidistant between the two anchor portions prior to and after reduction in length of members 32, as illustrated by comparing FIGS. 1 and 2. Plate 40 is initially positioned on bone segments 42 and 44 with the spreading apertures 38 used as guides for properly positioning the plate relative to a fracture. It is a simple matter to place the plate on the bone segments and to position apertures 38 generally along the fracture.

The distance that the compression member is foreshortened depends upon the width of the gap below the member, if any, and the amount of compression to be applied. In some cases, fractures may have a greater gap adjacent one bridge and a reduced gap adjacent another bridge so that compression members need be foreshortened different amounts in order to close the gap underlying the member. Furthermore, the strength of the bone and of the plate anchorage may vary so as to limit the appropriate amount of compression at various sites.

FIG. 5 is similar to FIG. 1 and illustrates a portion of second embodiment elongate bone plate 60. The plate 60 is manufactured using the same plate material and techniques previously described. Plate 60 includes a pair of elongate anchor portions 62 which extend longitudinally along opposite edges of the plate. Anchor portions 62 are like anchor portions 12 in plate 10. The anchor portions 62 are joined together by a plurality of spaced bridges 64 which extend between the inner strips of portions 62. Each bridge 64 includes a spring member 66 and a compression member 68 arranged in series extending laterally across the plate 60. Spring members 66 in plate 60 are like the spring members 30 in plate 10. Compression members 68 are like compression members 32 in plate 10. In each bridge the spring is joined to one of the anchor portions 62 and the compression member joined to the other anchor portion 62. As illustrated, the lateral positions of the spring and compression members may be reversed in adjacent bridges 64 and the spring members of alternate bridges joined to one anchor portion and spring members of the other bridges joined to the other anchor member.

Bone plates 70 are shaped for mounting on bone fractures and then applied to the bone segments to extend across fracture 72 as shown in FIG. 6. The bone plates are secured to the bone segments by pins or screws, as previously described.

After attachment of plate 70 across the bone fracture as shown in FIG. 6, the compression members 68 are spread along the length of the fracture to foreshorten the members permanently and close the fracture as shown in FIG. 7. The parallel strips of the compression members are bent to V-strips 78 which reduces the length of the bridges 64 sufficiently to close the gap 72 and elastically elongate or open the spring members 66 in each bridge. The spring members are elongated sufficiently to compensate for rebound lengthening of the compression members when the spreading tool is removed and to maintain a resilient force holding the segments together at closed fracture 72, as previously described. The resiliency of the elastically deformed spring members 66 holds the bone segments together to promote healing of the fracture without isolating the fracture from local stresses applied to the bone segments. In this way, healing of the fracture is promoted.

As in the first embodiment, the large number of mounting apertures provided in the anchor portions permit mounting of the plate 70 bone fragments located adjacent the fracture.

In plate 70, the spreading apertures 74 on opposite sides of the compression members are located different distances from the anchor portions 62, but still may be used to position the bone plate on the fracture prior to attaching the plate to the segments.

If desired, the bridges in plate 60 may be arranged with all of the spring members 66 joined to one of the anchor portions 62 and all of the compression members 68 joined to the other of the anchor portions.

Spring members 30, 66 extend when loaded by compression members 32, 68. Each spring member 30, 66 is a tension spring, that is, a spring that extends when loaded.

While I have illustrated and described the preferred embodiments of my invention, it is understood that this is capable of modification, and I therefore do not wish to be limited to the precise details set forth, but desire to avail myself of such changes and alterations as fall within the purview of the following claims.

What I claim as my invention is:

1. A bone plate comprising a pair of spaced anchor portions and a bridge extending between said portions, said bridge including a first elastic tension spring extendable along the bridge and an inelastic compression member permanently foreshortenable along the bridge, said spring and compression member arranged in series, whereby permanent foreshortening of the compression member elastically extends the spring.

2. A bone plate as in claim 1 wherein said anchor portions and bridge are formed from integral sheet metal.

3. A bone plate as in claim 1 wherein said spring and compression member each comprise a metal strip.

4. A bone plate as in claim 3 wherein said spring strip extends generally transverse to the bridge and said compression member strip extends generally along the bridge.

5. A bone plate as in claim 1 wherein said spring comprises a first pair of parallel strips joined together at the ends of the strips and extending generally transversely to the bridge, and the compression member comprises a second pair of parallel strips joined together at the ends of the strips and extending generally along the bridge.

6. A bone plate as in claim 5 wherein said compression member strips include spreading tool-engaging surfaces.

7. A bone plate as in claim 1 wherein said compression member includes a bendable strip having a surface adaptable for engagement by a bending tool.

8. A bone plate as in claim 1 including a second elastic tension spring in said bridge, said compression member located between said first and second springs.

9. A bone plate as in claim 1 wherein said compression member includes a pair of parallel bendable strips extending along the length of the bridge, said strips being joined together at the ends thereof and each including a central tool-engaging surface.

10. A bone plate as in claim 1 including a plurality of bridges extending between said anchor portions.

11. A bone plate as in claim 10 wherein each anchor portion includes a plurality of mounting apertures.

12. A bone plate as in claim 11 wherein each anchor portion includes a pair of spaced strips and rungs joining the strips, said strips and rungs defining openings in the anchor portions, said mounting apertures located at intersections of said strips and rungs.

13. A bone plate as in claim 12 wherein said anchor portions each include rung extensions extending from a strip and a mounting aperture in the end of each extension.

14. A bone plate as in claim 12 wherein each bridge is joined to each anchor portion at a rung.

15. A bone plate as in claim 1 wherein said anchor portions and bridge are formed from titanium sheet material.

16. A bone plate as in claim 1 wherein said bridge includes a single tension spring and a single compression member.

17. A bone plate as in claim 16 including a plurality of bridges and wherein alternate springs are joined to opposite anchor portions.

18. A bone plate as in claim 1 including a plurality of bridges and wherein said anchor portions and bridges are formed from a metal sheet.

19. A bone plate formed from an integral metal sheet, including a pair of spaced apart anchor portions, a plurality of mounting apertures in each of said anchor portions, a plurality of bridges extending between the anchor portions, each bridge including an elastic tension spring extendable along the bridge and a permanently deformable compression member foreshortenable along the bridge arranged in series, said compression member deformable to reduce the length of said bridge and elastically extend said tension spring to urge said anchor portions together.

20. A bone plate as in claim 19 wherein each tension spring includes an elastically deformable metal strip and each compression member includes a permanently bendable metal strip.

21. A bone plate as in claim 20 wherein each spring strip extends transversely to the bridge and each compression member strip extends generally along the bridge and is bendable to one side of the bridge.

22. A bone plate as in claim 21 wherein each tension spring includes a first pair of spaced, parallel elastically deformable strips joined at strip ends and each compression member includes a second pair of spaced parallel permanently bendable strips joined together at strip ends.

23. A bone plate as in claim 22 wherein said compression member strips each include spreading surfaces adapted to engage a spreading tool.

24. A bone plate as in claim 19 wherein each bridge includes a single compression member and a single tension spring.

25. A bone plate as in claim 19 wherein each bridge includes a pair of tension springs and a single compression member.

26. A bone plate as in claim 25 wherein in each bridge said compression member is located between a pair of tension springs.

27. A bone plate as in claim 19 wherein each anchor portion includes a pair of strips, rungs joining the strips, said mounting apertures located at intersections of said rungs and strips.

28. A bone plate as in claim 27 wherein said bridges join said anchor portions at rungs.

29. A bone plate as in claim 28 wherein the anchor portions each include rungs located between bridges.

30. A bone plate for compressing a bone fracture comprising a pair of spaced anchor portions, a bridge joining said anchor portions, said bridge including first means for elastically increasing the length of said bridge and second means for permanently foreshortening the length of said bridge, said first and second means arranged in series to draw said anchor portions towards one another and resiliently compress a bone fracture.

* * * * *